(12) United States Patent
Borchert et al.

(10) Patent No.: US 6,291,165 B1
(45) Date of Patent: Sep. 18, 2001

(54) SHUFFLING OF HETEROLOGOUS DNA SEQUENCES

(75) Inventors: Torben Vedel Borchert, Jyllinge (DK); Titus Kretzschmar, Munich (DE); Joel R. Cherry, Davis, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/040,025

(22) Filed: Mar. 17, 1998

Related U.S. Application Data
(60) Provisional application No. 60/044,920, filed on Apr. 25, 1997.

(30) Foreign Application Priority Data

| Mar. 18, 1997 | (DK) | 030/497 |
| Apr. 17, 1997 | (DK) | 043/297 |

(51) Int. Cl.[7] .................... C12Q 1/68; C12P 19/34
(52) U.S. Cl. .................. 435/6; 435/91.1; 435/91.2; 435/69.1; 435/463; 435/471
(58) Field of Search .............. 435/6, 91.1, 91.2, 435/69.1, 463, 471

(56) References Cited

U.S. PATENT DOCUMENTS

| 5,605,793 | * | 2/1997 | Stemmer | 435/6 |
| 5,811,238 | * | 9/1998 | Stemmer et al. | 435/6 |
| 5,830,721 | * | 11/1998 | Stemmer et al. | 435/172.1 |
| 5,837,458 | * | 11/1998 | Minshull et al. | 435/6 |

FOREIGN PATENT DOCUMENTS

| WO 95/17413 | 6/1995 | (WO) . |
| WO 95 22625 | 8/1995 | (WO) . |

OTHER PUBLICATIONS

Zhao et al., Nucleic Acids Res. 25(6), 1307–1308, 1997.*
Crameri et al., Nature 391, 288–291, 1998.*

* cited by examiner

*Primary Examiner*—Kenneth R. Horlick
(74) *Attorney, Agent, or Firm*—Steve T. Zelson; Valeta Gregg

(57) ABSTRACT

The present invention relates to a new method of shuffling especially heterologous polynucleotide sequences, screening and/or selection of new recombinant proteins resulting therefrom having a desired biological activity, and especially to production and identification of novel proteases exhibiting desired properties.

24 Claims, 8 Drawing Sheets

```
  1  M M R - K K S F W L G M L T A F M L V F T M A F S D S A S A   A13050_1.PRO
  1  M - K - K P L G K I V A S T A L L I S - - V A F S S I A S     A22550.PRO
  1  M - R - Q S L K V M V L S T - - - V A - - L L F M A N P A A   D26542.PRO
  1  M - R - G K K V W I S L L F A L A L I F T M A F G S T S S A   P00782.PRO
  1  M - K F K K I A A L S L A T S L A L F - - P A F G G S S L A   PD498.PRO

30  A Q P - - - - - - - A K - N V E K - - - - - - D - Y I V G F   A13050_1.PRO
 27  A A E - - - - - - - E A - - - - K - - - - - - E K Y L I - -   A22550.PRO
 24  A S E - - - - - - - E K - - - - K - - - - - - E - Y L I - -   D26542.PRO
 29  Q A A - - - - - - - G K S N G E K - - - - - - K - Y I V G F   P00782.PRO
 28  K E A P K P F Q P I N K - T L D K G A F E S G E - V I V K F   PD498.PRO

45  K S G - - - - - - - - - - - - - V K - - T - - A S V K K D     A13050_1.PRO
 38  - - - G F N E Q E A V S E F V E Q V E - - A N D E V A I L S   A22550.PRO
 34  - - - - - - - - - - - - - - - - V V - - E P E E V S A Q S     D26542.PRO
 45  K Q T - - - - - - - - - - - - - M S - - T M S A A K K K D     P00782.PRO
 56  K D G - - - - - - - - - - - - - V S K K A Q G S A L N K A     PD498.PRO

57  I I K E S G G K V D K Q F R I I N A A K A K L D K E A L K E   A13050_1.PRO
 63  E E E V E I E L L H E F E T I P V L S V E L S P E D V D A     A22550.PRO
 45  V E E S Y D V D V I H E F E E I P V I H A E L T K K E L K K   D26542.PRO
 59  V I S E K G G K V Q K Q F K Y V D A A S A T L N E K A V K E   P00782.PRO
 72  E A N E Q K A S A K D P F Q V L E V A D V - - - D Q A V K A   PD498.PRO

87  V K N D P D V A Y V E E D - - - - - - - H V A H A L Q T V     A13050_1.PRO
 93  L E L D P A I S Y I E E D - - - - - - - A E V T T M A Q S V   A22550.PRO
 75  L K K D P N V K A I E E N - - - - - - - A E V T - I S Q T V   D26542.PRO
 89  L K K D P S V A Y V E E D - - - - - - - H V A H A Y A Q S V   P00782.PRO
 99  L E N N P N V E Y A E P N Y T F Q A T W S P N D P Y Y S A Y   PD498.PRO

110  P Y G I P L I K A D K V Q A Q G F K G A N V K V A V L D T G   A13050_1.PRO
116  P W G I S R V Q A P A A H N R G L T G S G V K V A V L D T G   A22550.PRO
 97  P W G I S F I N T Q Q A H N R G I F G N A R V A V L D T G     D26542.PRO
112  P Y G V S Q I K A P A L H S Q G Y T G S N V K V A V I D S G   P00782.PRO
129  Q Y G P Q N T S T P A A W D V T R G S S T Q T V A V L D S G   PD498.PRO

140  I Q A S H P D L - - N V V G G A S F V A G E A Y N - T D G N   A13050_1.PRO
146  I - S T H P D L - - N I R G G A S F V P G E P S T - Q D G N   A22550.PRO
127  I - A S H P D L - - R I A G G A S F I S S E P S Y - H D N N   D26542.PRO
142  I D S S H P D L - - K V A G G A S M V P S E T N P F Q D N N   P00782.PRO
159  V D Y N H P D L A R K V I K G Y D F I D R D N N P - M D L N   PD498.PRO

167  G H G T H V A G T V A A - L D N T T G V L G V A P S V S L Y   A13050_1.PRO
172  G H G T H V A G T I A A - L N N S I G V L G V A P S A E L Y   A22550.PRO
153  G H G T H V A G T I A A - L N N S I G V L G V A P S A D L Y   D26542.PRO
170  S H G T H V A G T V A A - L N N S I G V L G V A P S A S L Y   P00782.PRO
188  G H G T H V A G T V A A D T N N G I G V A G M A P D T K I L   PD498.PRO

196  A V K V L N S S G S G S Y S G I V S G I E W A T T N G M D V   A13050_1.PRO
201  A V K V L G A S G S G S V S S I A Q G L E W A G N N G M H V   A22550.PRO
182  A V K V L D R N G S G S L A S V A Q G I E W A I N N N M H I   D26542.PRO
199  A V K V L G A D G S G Q Y S W I I N G I E W A I A N N M D V   P00782.PRO
218  A V R V L D A N G S G S L D S I A S G I R Y A A D Q G A K V   PD498.PRO
```

Fig. 2 (a)

```
226 I N M S L G G A S G S T A M K Q A V D N A Y A R G V V V A    A13050_1.PRO
231 A N L S L G S P S P S A T L E Q A V N S A T S R G V L V V A  A22550.PRO
212 I N M S L G S T S G S S T L E L A V N R A N N A G I L L V G  D26542.PRO
229 I N M S L G G P S G S A A L K A A V D K A V A S G V V V A    P00782.PRO
248 L N L S L G C E C N S T T L K S A V D Y A W N K G A V V V A  PD498.PRO

256 A A G N S G S S G N T N T I G Y P A K Y D S V I A V G A V D  A13050_1.PRO
261 A S G N S G A G S I S - - - - Y P A R Y A N A M A V G A T D  A22550.PRO
242 A A G N T G R Q G V N - - - - Y P A R Y S G V M A V A A V D  D26542.PRO
259 A A G N E G T S G S S S T V G Y P G K Y P S V I A V G A V D  P00782.PRO
278 A A G N D N V S R T F - - - - Q P A S Y P N A I A V G A I D  PD498.PRO

286 S N S N R A S F S S V G A E L E V M A P G A G V Y S T Y P T  A13050_1.PRO
287 Q N N N R A S F S Q Y G A G L D I V A P G V N V Q S T Y P G  A22550.PRO
268 Q N G Q R A S F S T Y G P E I E I S A P G V N V N S T Y T G  D26542.PRO
289 S S N Q R A S F S S V G P E L D V M A P G V S I Q S T L P G  P00782.PRO
304 S N D R K A S F S N Y G T W V D V T A P G V N I A S T V P N  PD498.PRO

316 N T Y A T L N G T S M A S P H V A G A A A L I L S K H P N L  A13050_1.PRO
317 S T Y A S L N G T S M A T P H V A G A A A L V K Q K N P S W  A22550.PRO
298 N R Y V S L S G T S M A T P H V A G V A A L V K S R Y P S Y  D26542.PRO
319 N K Y G A Y N G T S M A S P H V A G A A A L I L S K H P N W  P00782.PRO
334 N G Y S Y M S G T S M A S P H V A G L A A L L A S Q - - G K  PD498.PRO

346 S A S Q V R N R L S S T A T Y L - - - G S S F Y G K G L I    A13050_1.PRO
347 S N V Q I R N H L K N T A T S L - - - G S T N L Y G S G L V  A22550.PRO
328 T N N Q I R Q R I N Q T A T Y L - - - G S P S L Y G N G L V  D26542.PRO
349 T N T Q V R S S L E N T T K L - - - G D S F Y G K G L I      P00782.PRO
362 N N V Q I R Q A I E Q T A D K I S G T G T N F K Y G K - - I  PD498.PRO

373 N V E A A A Q                                                A13050_1.PRO
374 N A E A A T R                                                A22550.PRO
355 H A G R A T Q                                                D26542.PRO
376 N V Q A A A Q                                                P00782.PRO
390 N S N K A V R Y                                              PD498.PRO
```

Fig. 2 (b)

Percent Similarity

|   | 1 | 2 | 3 | 4 | 5 |   |
|---|---|---|---|---|---|---|
| 1 |   | 52.2 | 48.6 | 66.5 | 41.8 | 1 |
| 2 | 74.2 |   | 59.9 | 51.6 | 41.8 | 2 |
| 3 | 83.6 | 56.7 |   | 48.1 | 39.4 | 3 |
| 4 | 44.2 | 75.6 | 85.2 |   | 45.4 | 4 |
| 5 | 100.0 | 100.0 | 100.0 | 93.1 |   | 5 |
|   | 1 | 2 | 3 | 4 | 5 |   |

A13050_1.PRO
A22550.PRO
D26542.PRO
P00782.PRO
PD498.PRO

Fig. 2 (c)

```
LIP_RHIMI   MV-LKQRANY  LGF-LIVFFT  AFLVEAVPI-  -KRQSNSTV-  -----DSLPP    40
LIP_RHIDL   MVSFISISQG  VSLCLLVSSM  MLGSSAVPVS  GKSGSSNTAV  SASDNAALPP    50
ABSIDIA     M-----HSHF  VVLLLAVFIC  MCSVSGVPL-  -QIDPRDDK-  -----SYVPE    37
MDLA_PENCA  M--------R  LSFFTALSA-  ---VASLG--  ----------  ----YA-LPG    21
  Humicola  M--------R  SSL--VLFF-  ---VSAWT--  ----------  -----A-LAS    18
Consensus   M-----....  .SL.L.VF..  ...VSAVP.-  -.........  -----A.LP.    50

LIP_RHIMI   LIPSRTSAPS  SSPSTTDPEA  -P-AM-----  ---SRNGPLP  S--DVETKY-    77
LIP_RHIDL   LISSRCAPPS  NKGSKSDLQA  EPYNMQKNTE  WYESHGGNLT  SIGKRDDNLV   100
ABSIDIA     QYPLKVNGPL  PEGVSVIQGY  ----------  ---CENCTMY  P----EKN--    68
MDLA_PENCA  KLQSR-----  ----------  ----------  ----------  -----D----    27
  Humicola  PIR-R-----  ----------  ----------  ----------  -----E----    23
Consensus   .I.SR...P.  ..........  ----------  ---.......  .----E..--   100

LIP_RHIMI   -GMALNATSY  PDSVVQAMSI  ----DGG-IR  AATSQEINEL  TYYTTLSANS   121
LIP_RHIDL   GGMTLDLPSD  APPISLSSST  NSASDGGKVV  AATTAQIQEF  TKYAGIAATA   150
ABSIDIA     -----SVSAF  SSSSTQDYRI  ----------  -ASEAEIKAH  TFYTALSANA   102
MDLA_PENCA  ----------  ----------  ----------  -VSTSELDQF  EFWVQYAAAS    46
  Humicola  ----------  ----------  ----------  -VSQDLFNQF  NLFAQYSAAA    42
Consensus   ----.....   ..........  ----------  -AS..EI..F  T.Y...SA.A   150

LIP_RHIMI   YC---RTVIP  GATWDCI--H  C-DA-TEDLK  IIKTWS-TLI  YDTNAMVARG   163
LIP_RHIDL   YC---RSVVP  GNKWDCV--Q  C-QKWVPDGK  IITTFT-SLL  SDTNGYVLRS   193
ABSIDIA     YC---RTVIP  GGRWSCP--H  C-GV-ASNLQ  ITKTFS-TLI  TDTNVLVAVG   144
MDLA_PENCA  YYEADYTAQV  GDKLSCSKGN  CPEVEATGAT  VSYDFSDSTI  TDTAGYIAVD    96
  Humicola  YCGKNNDAPA  GTNITCTGNA  CPEVEKADAT  FLYSFEDSGV  GDVTGFLALD    92
Consensus   YC---RTV.P  G..W.C---.  C-.V...D..  I..TFS-SLI  .DTNG.VA..   200

LIP_RHIMI   DSEKTIYIVF  RGSSSIRNWI  ADLTFVPVSY  PPV-SGTKVH  KGFLDSYGEV   212
LIP_RHIDL   DKQKTIYLVF  RGTNSFRSAI  TDIVFNFSDY  KPV-KGAKVH  AGFLSSYEQV   242
ABSIDIA     EKEKTIYVVF  RGTSSIRNAI  ADIVFVPVNY  PPV-NGAKVH  KGFLDSYNEV   193
MDLA_PENCA  HTNSAVVLAF  RGSYSVRNWV  ADATF-VHTN  PGLCDGCLAE  LGFWSSWKLV   145
  Humicola  NTNKLIVLSF  RGSRSIENWI  GNLNFDLKEI  NDICSGCRGH  DGFTSSWRSV   142
Consensus   ...KTIYLVF  RGS.SIRNWI  AD..F....Y  PPV-.G.KVH  .GFLSSY..V   250

LIP_RHIMI   QNELVATVLD  QFKQYPSYKV  AVTGHSLGGA  TALLCALDLY  QREEGLSSSN   262
LIP_RHIDL   VNDYFPVVQE  QLTAHPTYKV  IVTGHSLGGA  QALLAGMDLY  QREPRLSPKN   292
ABSIDIA     QDKLVAEVKA  QLDRHPGYKI  VVTGHSLGGA  TAVLSALDLY  HHGH----AN   239
MDLA_PENCA  RDDIIKELKE  VVAQNPNYEL  VVVGHSLGAA  VATLAATDLR  GKGYP----S   191
  Humicola  ADTLRQKVED  AVREHPDYRV  VFTGHSLGGA  LATVAGADLR  GNGY-----D   187
Consensus   .D.L...V..  Q...HP.YKV  VVTGHSLGGA  .A.LAA.DLY  ..G..---.N   300

LIP_RHIMI   LFLYTQGQPR  VGDPAFANYV  VST-GIPYRR  TVNERDIVPH  LPPAAFGFLH   311
LIP_RHIDL   LSIFTVGGPR  VGNPTFAYYV  EST-GIPFQR  TVHKRDIVPH  VPPQSFGFLH   341
ABSIDIA     IEIYTQGQPR  IGTPAFANYV  IGT-KIPYQR  LVHERDIVPH  LPPGAFGFLH   288
MDLA_PENCA  AKLYAYASPR  VGNAALAKYI  TAQ--GNNFR  FTHTNDPVPK  LPLLSMGYVH   239
  Humicola  IDVFSYGAPR  VGNRAFAEFL  TVQTGGTLYR  ITHTNDIVPR  LPPREFGYSH   237
Consensus   ...YT.G.PR  VGNPAFA.YV  ..T-GIP..R  .VH.RDIVPH  LPP..FGFLH   350
```

Fig. 3 (a)

```
LIP_RHIMI    AGEEYWITDN  SPETVQVC-T  SDLET----S  DCSNSIVP-F  TSVLDHLSYF    355
LIP_RHIDL    PGVESWIKSG  TSN-VQIC-T  SEIET----K  DCSNSIVP-F  TSILDHLSYF    384
ABSIDIA      AGEEFWIMKD  SSLRV--C-P  NGIET----D  NCSNSIVP-F  TSVIDHLSYL    330
MDLA_PENCA   VSPEYWITSP  NNATVSTSDI  KVIDGDVSFD  GNTGTGLPLL  TDFEAHIWYF    289
  Humicola   SSPEYWIKSG  TLVPVTRNDI  VKIEG---ID  ATGGNNQPNI  PDIPAHLWYF    284
Consensus    .G.EYWI.S.  ....V..C-.  ..IET----D  .CSNSIVP-F  TS..DHLSYF    400
             .

LIP_RHIMI    GIN---TGLC  T-----  363
LIP_RHIDL    DIN---EGSC  L-----  392
ABSIDIA      DMN---TGLC  L-----  338
MDLA_PENCA   VQVDAGKGPG  LPFKRV  305
  Humicola   GLI----GTC  L-----  291
Consensus    ..N---.G.C  L-----  416
             .
```

Fig. 3 (b)

```
ABSIDIA      M-----HSHF  VVLLLAVFIC  MCSVSGVPL-  ----------  ------QIDP   28
LIP_RHIMI    MV-LKQRANY  LGF-LIVFFT  AFLVEAVPI-  -KRQSNSTV-  ------DSLPP  40
LIP_RHIDL    MVSFISISQG  VSLCLLVSSM  MLGSSAVPVS  GKSGSSNTAV  SASDNAALPP   50
Consensus    MV-....S..  V.L.L.VF..  M..VSAVP.-  -K...S..T.- ------..LPP  50

ABSIDIA      -RDDKSYVPE  QYPLKVN---  ----------  ------GPLP  EGVSVIQGYC   58
LIP_RHIMI    LIPSRTSAPS  SSPSTTDPEA  -P-AM-----  ---SRNGPLP  S--DVETKY-   77
LIP_RHIDL    LISSRCAPPS  NKGSKSDLQA  EPYNMQKNTE  WYESHGGNLT  SIGKRDDNLV   100
Consensus    LI.SR...PS  ..PSK.D..A  -P-.M-----  ---S..GPLP  S...V...Y.   100

ABSIDIA      ENCTMYPEKN  SVSAFSSSST  ----QD--YR  IASEAEIKAH  TFYTALSANA   102
LIP_RHIMI    -GMALNATSY  PDSVVQAMSI  ----DGG-IR  AATSQEINEL  TYYTTLSANS   121
LIP_RHIDL    GGMTLDLPSD  APPISLSSST  NSASDGGKVV  AATTAQIQEF  TKYAGIAATA   150
Consensus    .GMTL...S.  ...S...SSST ----DGG-.R  AAT.AEI.E.  T.YT.LSANA   150

ABSIDIA      YCRTVIPGGR  WSCPHCGV-A  SNLQITKTFS  TLITDTNVLV  AVGEKEKTIY   151
LIP_RHIMI    YCRTVIPGAT  WDCIHCDA-T  EDLKIIKTWS  TLIYDTNAMV  ARGDSEKTIY   170
LIP_RHIDL    YCRSVVPGNK  WDCVQCQKWV  PDGKIITTFT  SLLSDTNGYV  LRSDKQKTIY   200
Consensus    YCRTVIPG..  WDC.HC..-.  .DLKIIKTFS  TLI.DTN..V  ARGDKEKTIY   200

ABSIDIA      VVFRGTSSIR  NAIADIVFVP  VNYPPVNGAK  VHKGFLDSYN  EVQDKLVAEV   201
LIP_RHIMI    IVFRGSSSIR  NWIADLTFVP  VSYPPVSGTK  VHKGFLDSYG  EVQNELVATV   220
LIP_RHIDL    LVFRGTNSFR  SAITDIVFNF  SDYKPVKGAK  VHAGFLSSYE  QVVNDYFPVV   250
Consensus    .VFRGTSSIR  NAIADIVFVP  V.YPPV.GAK  VHKGFLDSY.  EVQN.LVA.V   250

ABSIDIA      KAQLDRHPGY  KIVVTGHSLG  GATAVLSALD  LYHHGH----  ANIEIYTQGQ   247
LIP_RHIMI    LDQFKQYPSY  KVAVTGHSLG  GATALLCALD  LYQREEGLSS  SNLFLYTQGQ   270
LIP_RHIDL    QEQLTAHPTY  KVIVTGHSLG  GAQALLAGMD  LYQREPRLSP  KNLSIFTVGG   300
Consensus    ..QL..HP.Y  KV.VTGHSLG  GATALL.ALD  LYQRE..LS.  .NL.IYTQGQ   300

ABSIDIA      PRIGTPAFAN  YVIGTKIPYQ  RLVHERDIVP  HLPPGAFGFL  HAGEEFWIMK   297
LIP_RHIMI    PRVGDPAFAN  YVVSTGIPYR  RTVNERDIVP  HLPPAAFGFL  HAGEEYWITD   320
LIP_RHIDL    PRVGNPTFAY  YVESTGIPFQ  RTVHKRDIVP  HVPPQSFGFL  HPGVESWIKS   350
Consensus    PRVG.PAFAN  YV.STGIPYQ  RTVHERDIVP  HLPP.AFGFL  HAGEE.WI..   350

ABSIDIA      DSSLRV--CP  NGIETDNCSN  SIVPFTSVID  HLSYLDMNTG  LCL  338
LIP_RHIMI    NSPETVQVCT  SDLETSDCSN  SIVPFTSVLD  HLSYGINTG   LCT  363
LIP_RHIDL    GTSN-VQICT  SEIETKDCSN  SIVPFTSILD  HLSYFDINEG  SCL  392
Consensus    .SS..VQ.CT  S.IET.DCSN  SIVPFTSVLD  HLSYFDINTG  LCL  393
```

Fig. 3 (c)

```
Humicola    MRSSL--VLF  FVSAWT-ALA  SPIR-REVSQ  DLFNQFNLFA  QYSAAAYCGK   46
MDLA_PENCA  MRLSFFTALS  AVASLGYALP  GKLQSRDVST  SELDQFEFWV  QYAAASYYEA   50
Consensus   MR.S....L.  .V.....AL.  .....R.VS.  ....QF....  QY.AA.Y...   50
            .. .        . .         . ..        ..          . .       .

Humicola    NNDAPAGTNI  TCTGNACPEV  EKADATFLYS  FEDSGVGDVT  GFLALDNTNK   96
MDLA_PENCA  DYTAQVGDKL  SCSKGNCPEV  EATGATVSYD  FSDSTITDTA  GYIAVDHTNS  100
Consensus   ...A..G...  .C....CPEV  E...AT..Y.  F.DS...D..  G..A.D.TN.  100
            .. .        . .         . ..        . ..        .. . .    .

Humicola    LIVLSFRGSR  SIENWIGNLN  FDLKEINDIC  SGCRGHDGFT  SSWRSVADTL  146
MDLA_PENCA  AVVLAFRGSY  SVRNWVADAT  F-VHTNPGLC  DGCLAELGFW  SSWKLVRDDI  149
Consensus   ..VL.FRGS.  S..NW.....  F........C  .GC....GF.  SSW..V.D..  150
            .. .        . .         . ..        . ..        .. . .    .

Humicola    RQKVEDAVRE  HPDYRVVFTG  HSLGGALATV  AGADLRGNGY  -DIDVFSYGA  195
MDLA_PENCA  IKELKEVVAQ  NPNYELVVVG  HSLGAAVATL  AATDLRGKGY  PSAKLYAYAS  199
Consensus   .......V..  .P.Y..V..G  HSLG.A.AT.  A..DLRG.GY  .......Y..  200
            .. .        . .         . ..        . ..        .. . .    .

Humicola    PRVGNRAFAE  FLTVQTGGTL  YRITHTNDIV  PRLPPREFGY  SHSSPEYWIK  245
MDLA_PENCA  PRVGNAALAK  YITAQ--GNN  FRFTHTNDPV  PKLPLLSMGY  VHVSPEYWIT  247
Consensus   PRVGN.A.A.  ...T.Q..G..  .R.THTND.V  P.LP....GY  .H.SPEYWI.  250
            .. .        . .         . ..        . ..        .. . .    .

Humicola    SGTLVPVTRN  DIVKIEG---  IDATGGNNQP  NIPDIPAHLW  YFGLI----G  288
MDLA_PENCA  SPNNATVSTS  DIKVIDGDVS  FDGNTGTGLP  LLTDFEAHIW  YFVQVDAGKG  297
Consensus   S.....V...  DI..I.G...  .D...G...P  ...D..AH.W  YF.......G  300
            .. .        . .         . ..        . ..        .. . .    .

Humicola    TCL-----    291
MDLA_PENCA  PGLPFKRV    305
Consensus   ..L.....    308
            .. .
```

Fig. 3 (d)

SHUFFLING OF HETEROLOGOUS DNA SEQUENCES

CROSS-REFERENCE TO RELATED APPLICATIONS

This application claims priority under 35 U.S.C. 119 of Danish applications 0304/97 filed Mar. 18, 1997, 0432/97 filed Apr. 17, 1997, and U.S. provisional application Ser. No. 60/044,920, the contents of which are fully incorporated herein by reference.

FIELD OF THE INVENTION

The present invention relates to a new method of shuffling especially heterologous polynucleotide sequences, screening and/or selection of new recombinant proteins resulting therefrom having a desired biological activity, and especially to production and identification of novel proteases exhibiting desired properties.

BACKGROUND OF THE INVENTION

It is generally found that a protein performing a certain bioactivity exhibits a certain variation between genera, and even between members of the same species differences may exist. This variation is even more outspoken at the genomic level.

This natural genetic diversity among genes coding for proteins having basically the same bioactivity has been generated in nature over billions of years and reflects a natural optimisation of the proteins coded for in respect of the environment of the organism in question.

However in general it has been found that the naturally occurring bioactive molecules are not optimized for the various uses to which they are put by mankind, especially when they are used for industrial purposes.

It has therefore been of interest to industry to identify such bioactive proteins that exhibit optimal properties in respect of the use to which it is intended.

This has for many years been done by screening of natural sources, or by use of mutagenesis. For instance, within the technical field of enzymes for use in e.g. detergents, the washing and/or dishwashing performance of e.g. naturally occurring proteases, lipases, amylases and cellulases have been improved significantly, by in vitro modifications of the enzymes.

In most cases these improvements have been obtained by site-directed mutagenesis resulting in substitution, deletion or insertion of specific amino acid residues which have been chosen either on the basis of their type or on the basis of their location in the secondary or tertiary structure of the mature enzyme (see for instance U.S. Pat. No. 4,518,584).

PRIOR ART

Numerous methods to create genetic diversity, such as by site directed or random mutagenesis, have been proposed and described in both the scientific literature and in patent applications. For further details in this respect reference is made to the related art section of WO 95/22625, wherein a review is provided.

One method for the shuffling of homologous DNA sequences has been described by Stemmer (Stemmer, (1994), Proc. Natl. Acad. Sci. USA, Vol. 91, 10747–10751; Stemmer, (1994), Nature, vol. 370, 389–391). The method concerns shuffling homologous DNA sequences by using in vitro PCR techniques. Positive recombinant genes containing shuffled DNA sequences are selected from a DNA library based on the improved function of the expressed proteins.

WO 95/22625 is believed to be the most pertinent reference in relation to the present invention in its "gene shuffling" aspect. WO 95/22625 relates to a method for shuffling of homologous DNA sequences. An important step in the method described in WO 95/22625 is to cleave the homologous template double-stranded polynucleotide into random fragments of a desired size followed by homologously reassembling of the fragments into full-length genes.

A disadvantage inherent to the method of WO 95/22625 is, however, that the diversity generated through that method is limited due to the use of homologous gene sequences (as defined in WO 95/22625).

Another disadvantage in the method of WO 95/22625 lies in the production of the random fragments by the cleavage of the template double-stranded polynucleotide.

A further reference of interest is WO 95/17413 describing a method of gene or DNA shuffling by recombination of DNA sequences either by recombination of synthesized double-stranded fragments or recombination of PCR generated sequences. According to the method described in WO 95/17413 the recombination has to be performed among DNA sequences with sufficient sequence homology to enable hybridization of the different sequences to be recombined.

WO 95/17413 therefore also entails the disadvantage that the diversity generated is relatively limited.

The present invention do not contain any steps involving production of random fragments by the cleavage of the template double-stranded polynucleotide, as described in WO 95/22625.

Further WO 95/22625 relates to shuffling of homologous, where the present invention relates to shuffling of heterologous genes.

SUMMARY OF THE INVENTION

The problem to be solved by the present invention is to avoid the limitation of shuffling only homologous DNA sequences by providing a method to shuffle/recombine heterologous sequences of interest.

The solution is to use at least one "conserved sequence region", wherein there is sufficient degree of homology between the heterologous sequences to be shuffled, as a "linking point" between said heterologous sequences.

Accordingly, a first aspect of the invention relates to a method for shuffling of heterologous sequences of interest comprising the following steps, i) identification of at least one conserved region between the heterologous sequences of interest;

ii) generating fragments of each of the heterologous sequences of interest, wherein said fragments comprise the conserved region(s); and iii) shuffling/recombining said fragments using the conserved region(s) as (a) homologous linking point(s).

In an second aspect the invention relates to a method for producing a shuffled protein having a desired biological activity comprising in addition to the steps of the first aspect the further steps:

iv) expressing the numerous different recombinant proteins encoded by the numerous different shuffled sequences from step iii); and v) screen or select the numerous different recombinant proteins from step ii) in a suitable screening or selection system for one or more recombinant protein(s) having a desired activity.

The term "conserved region" denotes a sequence region (preferably of at least 10 bp), wherein there is a relatively high sequence identity between said heterologous sequences.

In order for the conserved region to be used as "linking point" between said heterologous sequences, the sequence identity between the heterologous sequences, within said conserved regions, is as high as it enables hybridization of the heterologous sequences using said conserved region as hybridization point ("linking point").

BRIEF DESCRIPTION OF DRAWINGS

FIG. 1 illustrates the general concept of the invention, where
a) the black boxes defines mutual common conserved regions of the sequences of interest, and
b) the PCR primers named "a,a',b,b',etc." are primers directed to the conserved regions. Primers ("a'" and "b") ("b'" and "c") etc. are having a sequence overlap of preferably at least 10 bp, and
c) primers "z" and "z'" are primers directed to the flanking parts of the sequence area of the sequences of interest which are shuffled according to the method of the invention.

FIGS. 2a–2c: Show an alignment of 5 protease (subtilase) DNA sequences. Herein are a number of conserved regions such as the common partial sequences numbered 1–5.

FIGS. 3a–3d: Show an alignment of different lipases.

DEFINITIONS

Figure 1:
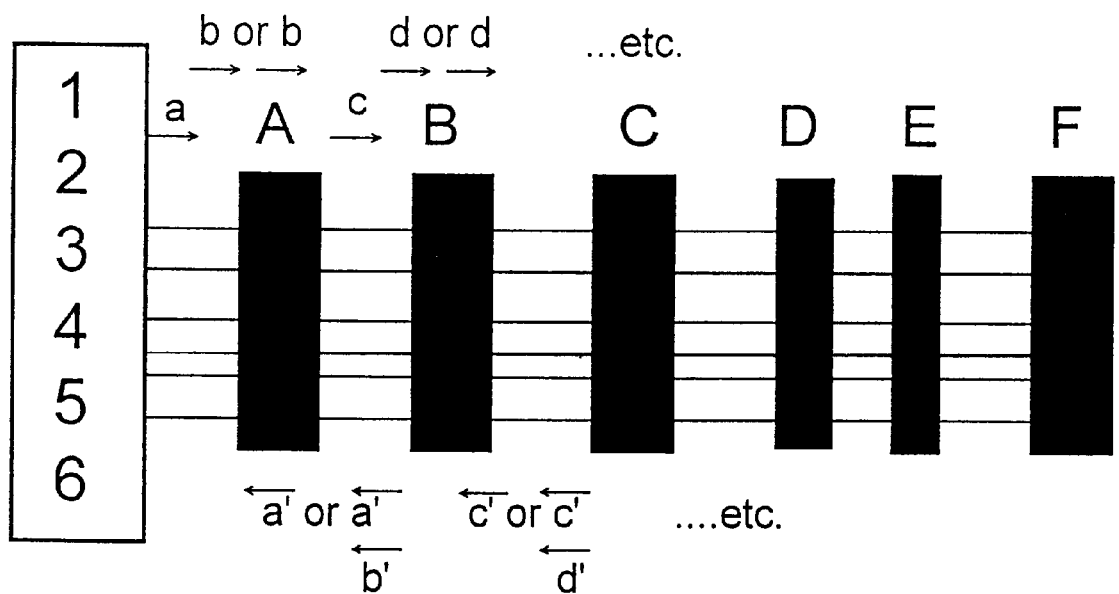
FIG. 1.

Prior to discussing this invention in further detail, the following terms will first be defined.

"Shuffling": The term "shuffling" means recombination of nucleotide sequence(s) between two or more DNA sequences of interest resulting in output DNA sequences (i.e. DNA sequences having been subjected to a shuffling cycle) having a number of nucleotides exchanged, in comparison to the input DNA sequences (i.e. starting point DNA sequences of interest).

Alternatively the term "shuffling" may be termed "recombining".

"Homology of DNA sequences" In the present context the degree of DNA sequence homology is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453).

"Homologous": The term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later (vide infra).

Using the computer program GAP (vide supra) with the following settings for DNA sequence comparison: GAP creation penalty of 5.0 and GAP extension penalty of 0.3, it is in the present context believed that two DNA sequences will be able to hybridize (using medium stringency hybridization conditions as defined below) if they mutually exhibit a degree of identity of at least 50%, more preferably at least 60%, more preferably at least 70%, more preferably at least 80%, more preferably at least 85%, and even more preferably at least 90%.

"heterologous": Two DNA sequences are said to be heterologous if one of them comprises a partial sequence of at least 40 bp which does not exhibit a degree of identity of more than 50%, more preferably of more than 70%, more preferably of more than 80%, more preferably of more than 85%, more preferably of more than 90%, and even more preferably of more than 95%, of any partial sequence in the other. More preferably the first partial sequence are al least 60 bp, more preferably the first partial sequence are al least 80 bp, even more preferably the first partial sequence are al least 120 bp, and most preferably the first partial sequence are al least 500 bp.

"Hybridization:" Suitable experimental conditions for determining if two or more DNA sequences of interest do hybridize or not is herein defined as hybridization at medium stringency as described in detail below.

A suitable experimental low stringency hybridization protocol between two DNA sequences of interest involves presoaking of a filter containing the DNA fragments to hybridize in 5× SSC (Sodium chloride/Sodium citrate, Sambrook et al. 1989) for 10 min, and prehybridization of the filter in a solution of 5× SSC, 5× Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity >1×10$^9$ cpm/μg ) probe (DNA sequence) for 12 hours at ca. 45° C. The filter is then washed twice for 30 minutes in 2× SSC, 0.5% SDS at least 55° C., more preferably at least 60° C., and even more preferably at least 65° C. (high stringency).

Molecules to which the oligonucleotide probe hybridizes under these conditions are detected using a x-ray film.

"Alignment": The term "alignment" used herein in connection with a alignment of a number of DNA and/or amino acid sequences means that the sequences of interest is aligned in order to identify mutual/common sequences of homology/identity between the sequences of interest. This procedure is used to identify common "conserved regions" (vide infra), between sequences of interest. An aligment may suitably be determined by means of computer programs known in the art, such as PILEUP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453).

"Conserved regions:" The term "conserved region" used herein in connection with a "conserved region" between DNA and/or amino acid sequences of interest means a mutual common sequence region of two or more sequences of interest, wherein there is a relatively high degree of sequence identity between two or more of the heterologous sequences of interest. In the present context a conserved region is preferably at least 10 base pairs (bp), more preferably at least 20 bp, and even more preferably at least 30 bp.

Using the computer program GAP (vide supra) with the following settings for DNA sequence comparison: GAP creation penalty of 5.0 and GAP extension penalty of 0.3, the degree of DNA sequence identity within the conserved region, between two or more of the heterologous sequences of interest, is preferably of at least 80%, more preferably at least 85%, more preferably at least 90%, and even more preferably at least 95%.

"primer": The term "primer" used herein especially in connection with a PCR reaction is a primer (especially a "PCR-primer") defined and constructed according to general standard specification known in the art ("PCR A practical approach" IRL Press, (1991)).

"A primer directed to a sequence:" The term "a primer directed to a sequence" means that the primer (preferably to be used in a PCR reaction) is constructed so it exhibits at least 80% degree of sequence identity to the sequence part of interest, more preferably at least 90% degree of sequence identity to the sequence part of interest, which said primer consequently is "directed to".

"Sequence overlap extension PCR reaction (SOE-PCR)": The term "SOE-PCR" is a standard PCR reaction protocol known in the art, and is in the present context defined and performed according to standard protocols defined in the art ("PCR A practical approach" IRL Press, (1991)).

"Flanking" The term "flanking" used herein in connection with DNA sequences comprised in a PCR-fragment means the most end partial sequences of the PCR-fragment, both in the 5' and 3' ends of the PCR fragment.

"Subtilases" A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271–272).

The bacterial serine proteases have molecular weights in the 20,000 to 45,000 Daltons range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) Bacteriological Rev. 41 711–753).

A sub-group of the serine proteases tentatively designated subtilases has been proposed by Siezen et al., Protein Engng. 4 (1991) 719–737. They are defined by homology analysis of more than 40 amino acid sequences of serine proteases previously referred to as subtilisin-like proteases.

DETAILED DESCRIPTION OF THE INVENTION

A method for shuffling heterologous sequences of interest

In a preferred embodiment the fragments generated in step ii) of the first aspect of the invention is generated by use of PCR technology.

Accordingly, in an embodiment of the invention relates to a method for shuffling of heterologous DNA sequences of interest, according to the first aspect of the invention, comprising the following steps i) identification of one or more conserved region(s) (hereafter named "A,B,C" etc.) in two or more of the heterologous sequences;

ii) construction of at least two sets of PCR primers (each set comprising a sense and an anti-sense primer) for one or more conserved region(s) identified in i) wherein in one set the sense primer (named: "a"=sense primer) is directed to a sequence region 5' (sense strand) of said conserved region (e.g. conserved region "A"), and the anti-sense primer (named "a'"=anti-sense primer) is directed either to a sequence region 3' (sense strand) of said conserved region or directed to a sequence region at least partially within said conserved region, and in the second set the sense primer (named: "b"=sense primer) is directed either to a sequence region 5' (sense strand) of said conserved region or directed to a sequence region at least partially within said conserved region and the anti-sense primer (named: "b'"=anti-sense primer) is directed to a sequence region 3' (sense strand) of said conserved region (e.g. conserved region "A"), and the two sequence regions defined by the regions between primer set "a" and "a'" and "b" and "b'" (both said regions is including the actual primer sequences) have a homologous sequence overlap of at least 10 base pairs (bp) within the conserved region;

iii) for one or more identified conserved region of interest in step i) two PCR amplification reactions are performed with the heterologous DNA sequences in step i) as template, and where one of the PCR reactions is using the 5' primer set identified in step ii) (e.g. named "a","a'") and the second PCR reaction is using the 3' primer set identified in step ii) (e.g. named "b","b'");

iv) isolation of the PCR fragments generated as described in step iii) for one or more of the identified conserved region in step i);

v) pooling of two or more isolated PCR fragments from step iv) and performance of a Sequence overlap extension PCR reaction (SOE-PCR) using said isolated PCR fragments as templates; and vi) isolation of the PCR fragment obtained in step v), wherein said isolated PCR fragment comprise numerous different shuffled sequences containing a shuffled mixture of the PCR fragments isolated in step iv), wherein said shuffled sequences is characterized in that the partial DNA sequences, originating from the homologous sequence overlaps in step ii), have at least 80% identity to one or more partial sequences in one or more of the original heterologous DNA sequences in step i).

A method for producing one or more recombinant protein(s) having a desired biological activity In an second aspect the invention relates to a method for producing a shuffled protein having a desired biological activity comprising in addition to the steps i) to vi) immediately above the further steps:

vii) expressing the numerous different recombinant proteins encoded by the numerous different the shuffled sequences in step vi); and viii) screen or select the numerous different recombinant proteins from step vii) in a suitable screening or selection system for one or more recombinant protein(s) having a desired activity.

Heterologous DNA sequences

The method of the present invention may be used to shuffle basically all heterologous DNA sequences of interest.

Preferably it is used to shuffle heterologous DNA sequences encoding a enzymatic activity such as an amylase, lipase, cutinase, cellulase, oxidase, phytase, and protease activity.

An further advantage of the present method, is it makes it possible to shuffle heterologous sequences encoding different activities, e.g. different enzymatic activities.

The method of the invention is in particular suitable to shuffle heterologous DNA sequences encoding a protease activity, in particular a subtilase activity.

A number of subtilase DNA sequences are published in the art. A number of those subtilase DNA sequences are in the present context heterologous DNA sequences, and it is generally believed that they are mutually too heterologous to be shuffled by the shuffling methods presently known in the art (WO 95/17413, WO 95/22625). However the method according to the invention enable shuffling of such sequences. For further details reference is made to a working example herein (vide infra).

Further the present invention is suitable to shuffle different lipase sequences. For further details reference is made to a working example herein (vide infra).

The heterologous DNA sequences used as templates may beforehand have been cloned into suitable vectors, such as a plasmid. Alternatively a PCR-reaction may be performed directly on microorganisms known to comprise the DNA sequence of interest according to standard PCR protocols known in the art.

Identification of one or more conserved regions in heterologous sequences:

Identification of conserved regions may be done by an alignment of the heterologous sequences by standard computer programs (vide supra).

Alternatively the method may be performed on completely new sequences, where the relevant "conserved regions" are chosen as conserved regions which are known in the art to be conserved regions for this particular class of proteins.

E.g. the method may be used to shuffle completely unknown subtilase sequences, which are known to be very conserved in e.g. regions around the active site amino acids. PCR reaction may then be performed directly on new unknown strains with primers directed to those conserved regions.

PCR-primers

The PCR primers are constructed according to the standard descriptions in the art. Preferably they are 10–75 base-pairs (bp) long.

Homologous sequence overlap

In step ii) of the invention the two sequence regions defined by the regions between primer set "a" and "a'" and "b" and "b'" (both said regions is including the actual primer sequences) have a homologous sequence overlap of at least 10 base pairs (bp) within the conserved region.

Said homologous sequence overlap is more preferably of at least 15 bp, ,more preferably of at least 20 bp, and even more preferably of at least 35 bp.

The homologous sequence overlaps in step ii) above is having at least 80% identity to one or more partial sequences is one or more of the original heterologous DNA sequences in step i) above, more preferably the homologous sequence overlaps in step ii) is having at least 90% identity to one or more partial sequences is one or more of the original heterologous DNA sequences in step i), and even more preferably the homologous sequence overlaps in step ii) is having at least 95% identity to one or more partial sequences is one or more of the original heterologous DNA sequences in step i) above.

PCR-reactions

If not otherwise mentioned the PCR-reaction performed according to the invention are performed according to standard protocols known in the art.

The term "Isolation of PCR fragment" is intended to cover as broad as simply an aliquot containing the PCR fragment. However preferably the PCR fragment is isolated to an extend which remove surplus of primers, nucleotide etc.

Further the fragment used for SOE-PCR in step v) above, may alternatively be generated by other processes than the PCR amplification process described in step iii) above. Suitable fragments used for the SOE-PCR in step v), may e.g. be generated by cutting out suitable fragments by restriction enzyme digestion at appropriate sites (e.g. restriction sites situated on each site of a conserved region identified in step i). Such alternative processes for generating such suitable fragments for use in the SOE-PCR in step v) are considered within the scope of the invention.

In an embodiment of the invention the PCR DNA fragment(s) is(are) prepared under conditions resulting in a low, medium or high random mutagenesis frequency.

To obtain low mutagenesis frequency the DNA sequence (s) (comprising the DNA fragment(s)) may be prepared by a standard PCR amplification method (U.S. Pat. No. 4,683, 202 or Saiki et al., (1988), Science 239, 487–491).

A medium or high mutagenesis frequency may be obtained by performing the PCR amplification under conditions which increase the misincorporation of nucleotides, for instance as described by Deshler, (1992), GATA 9(4), 103–106; Leung et al., (1989), Techique, Vol. 1, No. 1, 11–15.

Final shuffles sequences

One of the advantages of the present invention is that the final "shuffled sequences" in step vi) above of the present invention only comprise sequence information which is originally derived from the original heterologous sequences of interest in step i) above. The present invention do not use artificially made "linker sequences" to recombine one or more of the heterologous sequences, which is a strategy known in the art to e.g. be able to shuffle different domains in proteins, wherein each domain is encoded by different heterologous sequences (WO 95/17413).

Accordingly the invention relates to a method characterized in that in each of the shuffled sequences, the partial DNA sequences, originating from the homologous sequence overlaps in step ii), only contain sequence information which is originally derived from the original heterologous sequences in step i) (in first to third aspect of the invention) (i.e. said "homologous sequence overlaps in step ii) is having at least 80% identity to one or more partial sequences is one or more of the original heterologous DNA sequences in step i).

More preferably the "homologous sequence overlaps in step ii) is having at least 90% identity to one or more partial sequences is one or more of the original heterologous DNA sequences in step i); and even more preferably the "homologous sequence overlaps in step ii) is having at least 95% identity to one or more partial sequences is one or more of the original heterologous DNA sequences in step i), and even most preferably the "homologous sequence overlaps in step ii) is having 100% identity to one or more partial sequences is one or more of the original heterologous DNA sequences in step i).

Expressing the recombinant protein from the shuffled sequences

Expression the recombinant protein encoded by the shuffled sequence of the present invention may be performed by use of standard expression vectors and corresponding expression systems known in the art.

Suitable screening or selection system

In is second aspect the present invention relates to a method for producing one or more recombinant protein(s) having a desired biological activity.

A suitable screening or selection system will depend on the desired biological activity.

A number of suitable screening or selection systems to screen or select for a desired biological activity are described in the art. Examples are:

Strauberg et al. (Biotechnology 13: 669–673 (1995), which describe a screening system to screen for Subtilisin variants having a Calcium-independent stability;

Bryan et al. (Proteins 1:326–334 (1986)), which describe a screening assay to screen for Protease having a enhanced thermal stability; and PCT-DK96/00322 which describe a screening assay to screen for lipases which are having an improved wash performance in washing detergents.

An preferably embodiment of the invention comprise screening or selection of recombinant protein(s), wherein the desired biological activity is improved performance in a dish-wash or laundry detergents. Examples of suitable dish-wash or laundry detergent are disclosed in PCT-DK96/00322 and WO 95/30011.

The invention is described in further detail in the following examples which are not in any way intended to limit the scope of the invention.

Materials and Methods
Strains
*E. coli* strain: DH10B (Life Technologies)
*Bacillus subtilis* strain: DN1885 amyE. A derivative of B,s 168RUB200 (J. Bacteriology 172:4315–4321 (1990))
Plasmids
pKH400: pKH400 was constructed from pJS3 (*E. coli - B. subtilis* shuttle vector containing a synthetic gene encoding for subtilase 309 (described by Jacob Schiødt et al. in Protein and Peptide letters 3:39–44 (1996)), by introduction of two BamHI sites at positions 1841 and 3992.
Protease sequences used for shuffling
GenBank entries A13050_1, D26542, A22550, Swiss-Prot entry SUBT_BACAM P00782, and PD498 (Patent Application No. WO 96/34963).
General molecular biology methods:
Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, NY; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.
Enzymes for DNA manipulations
Unless otherwise mentioned all enzymes for DNA manipulations, such as e.g. restriction endonucleases, ligases etc., are obtained from New England Biolabs, Inc.

EXAMPLES

Example 1

A) Vector construction
1) Amplification of the pre-pro sequences

Host cells harboring the plasmid DNA encoding the full length enzymes A13050_1 (GenBank), SUBT_BACAM P00782 (Swiss-Prot), D26542 (GenBank), A22550 (GenBank), and PD498 (Patent Application No. WO 96/34963) were starting material. By standard mini-prep isolation of plasmid DNA, purified DNA was obtained. With these template DNAs, 5 standard PCRs were performed to amplify the respective pre-pro sequences. The fragments were generated using the proof reading Pwo DNA polymerase (Boehringer Mannheim) and the following sets of primers directed against the very N- and C-termini of the respective pre-pro sequences:

```
A13050_1
TiK111: 5' GAG GAG GGA AAC CGA ATG AGG AAA AAG AGT TTT TGG.    (SEQ ID NO:1)

TiK117: 5' CGC GGT CGG GTA CCG TTT GCG CCA AGG CAT G.          (SEQ ID NO:2)

SUBT_BACAM P00782
TiK112: 5' GAG GAG GGA AAC CGA ATG AGA GGC AAA AAA GTA TGG.    (SEQ ID NO:3)

TiK118: 5' CGC GGT CGG GTA CCG ACT GCG CGT ACG CAT G.          (SEQ ID NO:4)

D26542
TiK110: 5' GAG GAG GGA AAC CGA ATG AGA CAA AGT CTA AAA GTT ATG. (SEQ ID NO:5)

TiK116: 5' CGC GGT CGG GTA CCG TTT GAC TGA TGG TTA CTT C.      (SEQ ID NO:6)

A22550
TiK109: 5' GAG GAG GGA AAC CGA ATG AAG AAA CCG TTG GGG.        (SEQ ID NO:7)

TiK115: 5' CGC GGT CGG GTA CCG ATT GCG CCA TTG TCG TTA C.      (SEQ ID NO:8)

PD498
TiK113: 5' GAG GAG GGA AAC CGA ATG AAG TTC AAA AAA ATA GCC.    (SEQ ID NO:9)

TiK119: 5' CGC GGT CGG GTA CCG CAG AAT AGT AAG GGT CAT TC.     (SEQ ID NO:10)
```

The obtained DNA fragments of a length between 300–400 bp were purified by agarose gel-electrophoresis with subsequent gel extraction (QIAGEN) and subjected to assembly by splice-by-overlap extension PCR (SOE-PCR).

2) SOE-PCR

The pre-pro fragments were then separately spliced by SOE-PCR to the 3' part of the promoter of the vector pKH400. The 3' part of the promoter was obtained by standard PCR with the Pwo DNA polymerase using 1 ng of pKH400 as template and the primers:

```
TiK106: 5' CGA CGG CCA GCA TTG G.      (SEQ ID NO:11)

TiK107: 5' CAT TCG GTT TCC CTC CTC.    (SEQ ID NO:12)
```

The resulting 160 bp fragment was gel-purified. Subsequently, 5 SOE-PCRs were performed under standard conditions (Pwo DNA polymerase) using as template each of the 5 pre-pro sequences mixed with equal molar amounts of the 3' part of the promoter. The assembling primers were:

```
                                       (SEQ ID NO:13)
TiK120: 5' CTT TGA TAC GTT TAA ACT ACC.

(SEQ ID NO:14)
TiK121: 5' CGC GGT CGG GTA CCG.
```

The obtained fragments were also gel-purified.

3) Insertion of the pre-pro sequences into the pKH400 shuttle vector

The pKH400 vector was cut with Pme I and Acc65 I to remove the existing linker sequence. The 5 purified SOE-PCR fragments from 2) were also digested with the same enzymes and gel-purified. Only with the SOE-PCR of the SUBT_BACAM P00782 pre-pro sequence special caution was necessary because it contains an internal Pme I-site so that a partial digest was performed. In separate standard ligation mixes the pre-pro fragments were then ligated to the pKH400 vector. After transformation of DH10B *E. coli* cells, colonies were selected on ampicillin containing media. Correctly transformed cells were identified by control digest and sequenced. The thus obtained vectors were named pTK4001-4005.

B) Preparation of the small fragments of the proteases A13050_1 (GenBank), SUBT_BACAM P00782 (Swiss-Prot), D26542 (GenBank), A22550 (GenBank), and PD498 (Patent Application No. WO 96/34963).

1) Standard PCR reactions were assembled with 0.5 µl of mini-prep DNA of each protease gene as templates. Since these five protease genes shall be fragmented into six fragments (I–VI), 30 PCRs are required (see FIG. 1). The Ampli-Taq polymerase (5U) was used in combination with the following primer sets (the numbering corresponds to the amino acid position in A22550). If there are primers labeled #0.1, #0.2, etc., then equal molar amounts of them are mixed prior to PCR and treated as one primer in the PCR:

```
Set I)
TiK122.1 (116-124)
5' CCG GCG CAG GCG GTA CCX TRS GGX ATW XCX CXX RTX MAA GC.    (SEQ ID NO:15)

TiK122.2 (116-124)
5' CCG GCG CAG GCG GTA CCX TRS GGX ATW XCA WWC ATX WAT AC.    (SEQ ID NO:16)

TiK123 (174-180)
5' GTT CCX GCX ACR TGX GTX CC.                                (SEQ ID NO:17)

Set II)
TiK124 (174-180)
5' GGX ACX CAY GTX GCX GGA AC.                                (SEQ ID NO:18)

TiK125.1 (217-223)
5' GCC CAC TSX AKX CCG YTX AC.                                (SEQ ID NO:19)

TiK125.2 (217-223)
5' GCC CAC TSX AKX CCT YGX GC.                                (SEQ ID NO:20)

TiK125.3 (217-223)
5' GCC CAX TSR AKX CCK XXX RCW AT.                            (SEQ ID NO:21)

Set III)
TiK126.1 (217-223)
5' GTX ARC GGX MTX SAG TGG GC.                                (SEQ ID NO:22)

TiK126.2 (217-223)
5' GCX CRA GGX MTX SAG TGG GC.                                (SEQ ID NO:23)

TiK126.3 (217-223)
5' TWG CYC AAG GWW TXS AXT GKR.                               (SEQ ID NO:24)

TiK126.5 (217-223)
5' TWG CTC AAG GHH THS ART GG.                                (SEQ ID NO:25)

TiK127.1 (255-261)
5' GCX GCX ACX ACX ASX ACX CC.                                (SEQ ID NO:26)

TiK127.2 (255-261)
5' GCY SCW AYW AMX AGW AYA YCA.                               (SEQ ID NO:27)

Set IV)
TiK128.1 (255-261)
5' GGX GTX STX GTX GTX GCX GC.                                (SEQ ID NO:28)

TiK128.2 (255-261)
```

```
                                                -continued
5' TGR TRT WCT MKT WRT WGS RGC.                          (SEQ ID NO:29)

TiK129.1 (292-299)
5' GBX CCX ACR YTX GAR AAW GAX G.                        (SEQ ID NO:30)

TiK129.2 (292-299)
5' GBX CCR TAC TGX GAR AAR CTX G.                        (SEQ ID NO:31)

TiK129.3 (292-299)
5' GKX CCA TAC KKA GAR AAR YTT G.                        (SEQ ID NO:32)

TiK129.5 (292-299)
5' GKR CCA TAC KKA GAR AAG YTT G.                        (SEQ ID NO:33)

Set V)
TiK130.1 (292-299)
5' CXT CWT TYT CXA RYG TXG GXV C.                        (SEQ ID NO:34)

TiK130.2 (292-299)
5' CXA GYT TYT CXC AGT AYG GXV C.                        (SEQ ID NO:35)

TiK130.3 (292-299)
5' CAA GYT TCT CTM MGT ATG GSM C.                        (SEQ ID NO:36)

TiK130.5 (292-299)
5' CAA GTT TCT CTC AGT ATG GGA C.                        (SEQ ID NO:37)

TiK131.1 (324-330)
5' GGX GWX GCC ATX GAY GTX CC.                           (SEQ ID NO:38)

TiK131.2 (324-330)
5' GGA GTA GCC ATX GAX GTW CC.                           (SEQ ID NO:39)

Set VI)
TiK132.1 (324-330)
5' GGX ACR TCX ATG GCX WCX CC.                           (SEQ ID NO:40)

TiK132.2 (324-330)
5' GGW ACX TCX ATG GCA WCX CC.                           (SEQ ID NO:41)

TiK133.1 (375-380)
5' CGG CCC CGA CGC GTT TAC YGX RYX GCX SYY TSX RC.       (SEQ ID NO:42)

TiK133.2 (375-380)
5' CGG CCC CGA CGC GTT TAT CKT RYX GCX XXY TYW G.        (SEQ ID NO:43)

TiK133.3 (375-380)
5' CGG CCC CGA CGC GTT TAT CKT RCX GCX GCX TYT GMR TT.   (SEQ ID NO:44)

TiK133.4 (375-380)
5' CGG CCC CGA CGC GTT TAT CTT ACG GCA GCC TCA GC.       (SEQ ID NO:45)
```

(X=deoxy-inosine, Y=50% C+50% T, R=50% A+50% G, S=50% C+50% G, W=50% A+50% T, K=50% T+50% G, M=50% A+50% C, B=33.3% C+33.3% G+33.3% T, V=33.3% C+33.3% G+33.3% A, H=33.3% C+33.3% A+33.3%).

After 30 cycles at annealing temperatures ranging from 40–60° C. the amplified fragments were gel-purified and recovered.

2) SOE-PCR to randomly assemble the small fragments

Equimolar amounts of each of the purified fragments were taken and mixed in one tube as templates for assembly in an otherwise standard SOE-PCR with Ampli-Taq polymerase. The external primer used are:

```
TiK134.1: CCG GCG CAG GCG GTA CC.   (SEQ ID NO:46)
TiK135.1: CGG CCC CGA CGC GTT TA.   (SEQ ID NO:47)
```

Also the primers pairs

```
TiK134.2: GGC GCA GGC GGT AC.       (SEQ ID NO:48)
TiK135.2: GCC CCG ACG CGT TTA.      (SEQ ID NO:49)
``` and

```
TiK134.3: CGC AGG CGG TAC.          (SEQ ID NO:50)
TiK135.3: CCC GAC GCG TT.           (SEQ ID NO:51)
``` can be used. The annealing temperatures are ranging from 40° C. to 70° C.

The re-assembly is also achieved by sequentially re-assembling all conceivable combinations of fragments, e.g.: In tube 1 all seven fragments obtained by PCR with the primers of set I (see above, B1-2) are mixed, in tube 2 fragments obtained by PCR with the primers of set II are mixed, in tube 3 fragments obtained by PCR with the primers of set III are mixed, in tube 4 fragments obtained by PCR with the primers of set IV are mixed, in tube 5 fragments obtained by PCR with the primers of set V are mixed, in tube 6 fragments obtained by PCR with the primers of set VI are mixed.

Then, a SOE-PCR is performed by mixing aliquots of tube 1 and 2 and using the mix as template for a primary SOE-PCR with corresponding external primers. The same is performed with mixtures of aliquots of tube 3 and 4 as well as tube 5 and 6. The respective external primer pairs are TiK134.#/125.# for fragments 1 and 2, TiK126.#/129.# for fragments 3 and 4, and TiK 130.#/135.# for fragments 5 and 6. The amplified assembled fragments of about 340, 260, and 280 bp length, respectively, are purified by agarosegel electrophoresis. In a secondary SOE-PCR the obtained fragments are mixed and assembled using primer pair TiK134.#/135.# as external primers. The obtained full-length protease genes are gel-purified as described above.

In another example, aliquots of tubes 1, 2, and 3 are mixed and re-assembled by a primary SOE-PCR with primer pair TiK134.#/127.#. Aliquots of tubes 4, 5, and 6 are also mixed in another tube and re-assembled by another SOE-PCR using the primers TiK128.#/135.#. The generated fragments of about 450 bp length are purified as described above, mixed and reassembled in a secondary SOE-PCR with external primers TiK134.#/135.#. The obtained full-length protease genes are gel-purified as described above.

In principle every combination of fragments might be assembled in separate SOE-PCRs. In subsequent SOE-PCRs the obtained assembled units are assembled to larger units until the final full length gene is obtained. The overall number of SOE-PCRs used for that purpose is only limited by experimental capacity. The only prerequisite which is inherent to SOE-PCR is that the to be assembled fragments must contain a sequence overlap as defined earlier.

C) Cloning of the SOE-PCR-derived full-length protease-hybrids to yield library #1

The full-length protease-hybrid genes from step B2) as well as the newly constructed shuttle vectors pTK4001-4005 from A3) are separately digested with Acc65 I and Mlu I. In standard ligation procedures the protease genes are separately ligated to each of the five vectors pTK4001-4005 and transformed into *E. coli* DH10B. Selection of correctly transformed cells is performed with ampicillin. DNA of these clones is prepared and designated library #1. The library size is about $10^6$ independent transformants.

D) Screening of library #1

Aliquots of library #1 are used to transform Bacilli cells DN1885. The transformants are screened for the desired properties.

By this method using a standard protease activity assay to screen for the desired property in step D) above a number of new shuffled subtilisins with a desired property was identified.

Example 2

The same methods as described in example 1 can be used for amplification of PCR fragments from fungal lipases. The fungal lipases from the following fungi are aligned using the alignment program from Geneworks (using the following parameters:cost to open a gap=5, cost to lengthen a gap=25, Minimum Diagonal lLength=4, Maximum Diagonal Length=10, Consensus cutoff=50%): Rhizomucor Miehei (LIP_RHIMI from the Swiss Prot data base), Rhizopus Delemar (LIP_RHIDL from the Swiss Prot data base), *Penecillium camenbertii* (MDLA_PENCA from the Swiss Prot data base) Absidia reflexa (WO 96/13578) and *Humicola lanuginosa* (U.S. Pat. No. 5,536,661).

Primers for amplification of Absidia (Absidia), Rhizopus (LIP_RHIDL) and Rhizomucor (LIP_RHIMI) lipase genes for shuffling N: according to the IUPAC nomenclature means all 4 bases (A,T,G,C)

```
Set 1)
5' primer for YCRT/SVI/VPG:    TAY TGY MGR ACN GTN ATH CCN GG or    (SEQ ID NO:52)

TAY TGY MGR AGY/TCN GTN GTN CCN GG   (SEQ ID NO:53 and SEQ ID NO:54)

3' primer for VFRGT/S:         NSW NCC YCK RAA NAC                  (SEQ ID NO:55)

Set 2)
5' primer for VFRGT/S:         GTN TTY MGR GGN WSN                  (SEQ ID NO:56)

3' primer for KVHK/AGF:        RAA NCC YTT RTG NAC YTT or           (SEQ ID NO:57)

RAA NCC NGC RTG NAC YTT              (SEQ ID NO:58)

Set 3)
5' primer for KVHK/AGF:        AAR GTN CAY AAR GGN TTY or           (SEQ ID NO:59)

AAR GTN CAY GCN GGN TTY              (SEQ ID NO:60)

3' primer for VTGHSLGG:        CC NCC YAR NGA RTG NCC NGT NAC or    (SEQ ID NO:61)

CC NCC YAR RCT RTG NCC NGT NAC       (SEQ ID NO:62)

Set 4)
5' primer for VTGHSLGG:        GTN ACN GGN CAY TCN YTR GGN GG or    (SEQ ID NO:63)

GTN ACN GGN CAY AGY YTR GGN GG       (SEQ ID NO:64)

3' primer for FGFLH:           RTG YAR RAA NCC RAA                  (SEQ ID NO:65)
```

-continued

```
Set 5)
5' primer for FGFLH:      TTY GGN TTY YTR CAY         (SEQ ID NO:66)

3' primer for IVPFT:      NGT RAA NGG NAC DAT         (SEQ ID NO:67)
```

Primers for amplification of *Humicola lanuginosa* (Humicola) and *Penicillium camenbertii* (MDLA_PENCA) lipase genes for shuffling

```
Set 1)
5' primer for CPEVE:       TGY CCN GAR GTN GAR         (SEQ ID NO:68)

3' primer for VLS/AFRG:    NCC YCK RAA NGM YAR NAC     (SEQ ID NO:69)

Set 2)
5' primer for VLS/AFRG:    GTN YTR KCN TTY MGR GGN     (SEQ ID NO:70)

3' primer for GFT/WSSW:    CCA NGA NGA NGT RAA NCC or  (SEQ ID NO:71)
                           CCA RSW RSW CCA RAA NCC     (SEQ ID NO:72)

Set 3)
5' primer for GFT/WSSW:    GGN TTY ACN TCN TCN TGG or  (SEQ ID NO:73)
                           GGN TTY TGG WSY WSY TGG     (SEQ ID NO:74)

3' primer for GHSLGG/AA:   NGC NSC NCC YAR NGA RTG NCC or (SEQ ID NO:75)
                           NGC NSC NCC YAR RCT RTG NCC (SEQ ID NO:76)

Set 4)
5' primer for GHSLGG/AA:   GGN CAY TCN YTR GGN GSN GCN or (SEQ ID NO:77)
                           GGN CAY AGY YTR GGN GSN GCN (SEQ ID NO:78)

3' primer for PRVGN:       RTT NCC NAC YCK NGG         (SEQ ID NO:79)

Set 5)
5' primer for PRVGN:       CCN MGR GTN GGN AAY         (SEQ ID NO:80)

3' primer for THTND:       RTC RTT NGT RTG NGT         (SEQ ID NO:81)

Set 6)
5' primer for THTND:       ACN CAY ACN AAY GAY         (SEQ ID NO:82)

3' primer for PEYWI:       DAT CCA RTA YTC NGG         (SEQ ID NO:83)

Set 7)
5' primer for PEYWI:       CCN GAR TAY TGG ATH         (SEQ ID NO:84)

3' primer for AHL/IWYF:    RAA RTA CCA DAK RTG NGC     (SEQ ID NO:85)
```

Primers for shuffling of all five genes:

```
Set 1)
5' primer for AN/TA/SYCR: GCN AMY KCN TAY TGY MG                     (SEQ ID NO:86)

for Absidia, Rhizopus and Rhizomucor sequences

5' primer for AN/TA/SYCGKNNDA: GCN AMY KCN TAY TGY GGN AAR AAY AAY GAY GC  (SEQ ID NO:87)

for Humicola

5' primer for AN/TA/SYCEADYTA: GCN AMY KCN TAY TGY GAR GCN GAY TAY ACN GC  (SEQ ID NO:88)

for P. camenbertii
```

-continued

3' primer for E/QKTIY: RTA DAT NGT YTT YTS (SEQ ID NO:89)

for Absidia, Rhizopus and Rhizomucor sequences

3' primer for ALDNTE/QKTIY: RTA DAT NGT YTT YTS NGT RTT RTC YAR NGC (SEQ ID NO:90)

for Humicola

3' primer for AVDHTE/QKTIY: RTA DAT NGT YTT YTS NGT RTG RTC NAC NGC (SEQ ID NO:91)

for P. camenbertii

Set 2)
5' primer for E/QKTIY: SAR AAR ACN ATH TAY (SEQ ID NO:92)

for Absidia, Rhizopus and Rhizomucor sequences

5' primer for E/QKTIYLA/SFRG: SAR AAR ACN ATH TAY YTR KCN TTY MGR GGN (SEQ ID NO:93)

for the two other sequences

3' primer for KVHK/AGF: RAA NCC YTT RTG NAC YTT (SEQ ID NO:94)

or RAA NCC NGC RTG NAC YTT (SEQ ID NO:95)

for Absidia, Rhizopus and Rhizomucor sequences

3' primer for ICSGCKVHK/AGF: RAA NCC YTT RTG NAC YTT RCA NCC NGA RCA DAT (SEQ ID NO:96)

or RAA NCC NGC RTG NAC YTT RCA NCC NGA RCA DAT (SEQ ID NO:97)

for Humicola

3' primer for LCDGCKVHK/AGF: RAA NCC YTT RTG NAC YTT RCA NCC RTC RCA YAR (SEQ ID NO:98)

or RAA NCC NGC RTG NAC YTT RCA NCC RTC RCA YAR (SEQ ID NO:99)

for P. camenbertii

Set 3)
5' primer for KVHK/AGF: AAR GTN CAY AAR GGN TTY (SEQ ID NO:100)

or AAR GTN CAY GCN GGC TTY (SEQ ID NO:101)

for Absidia, Rhizopus and Rhizomucor sequences

5' primer for KVHK/AGFTSSW: AAR GTN CAY AAR GGN TTY ACN TCN TCN TGG (SEQ ID NO:102)

AAR GTN CAY GCN GGN TTY ACN TCN TCN TGG (SEQ ID NO:103)

for Humicola

5' primer for KVHK/AGFWSSW: AAR GTN CAY AAR GGN TTY TGG WSY WSY TGG (SEQ ID NO:104)

or AAR GTN CAY GCN GGN TTY TGG WSY WSY TGG (SEQ ID NO:105)

for P. camenbertii

3' primer for GHSLGG/AA: NGC NSC NCC YAR NGA RTG NCC (SEQ ID NO:106)

or NGC NSC NCC YAR RCT RTG NCC (SEQ ID NO:107)

for all five sequences

Set 4)
5' primer for GHSLGG/AA: GGN CAY TCN YTN GGN GSN GCN (SEQ ID NO:108)

or GGN CAY AGY YTN GGN GSN GCN (SEQ ID NO:109)

for all five sequences

3' primer for PRVGN/D: RTY NCC NAC YCK NGG (SEQ ID NO:110)

for all the genes except Absidia

3' primer for TQGQPRVGN/D: RTY NCC NAC YCK NGG YTG NCC YTG NGT (SEQ ID NO:111)

for Absidia

-continued

```
Set 5)
5' primer for PRVGN/D: CCN MGR GTN GGN RAY                              (SEQ ID NO:112)

for all the genes except Absidia

5' primer for PRVGN/DPAFA: CCN MGR GTN GGN RAY CCN GCN TTY GCN          (SEQ ID NO:113)

for Absidia

3' primer for RDIVPH/R/K: YK NGG NAC DAT RTC YCK                        (SEQ ID NO:114)

for Absidia, Rhizopus and Rhizomucor sequences

3' primer for I/FTHTRDIVPH/R/K: YK NGG NAC DAT RTC YCK NGT RTG NGT RAW  (SEQ ID NO:115)

for the two other sequences

Set 6)
5' primer for RDIVPH/R/K: MGR GAY ATH GTN CCN MR                        (SEQ ID NO:116)

for Absidia, Rhizopus and Rhizomucor sequences

5' primer for RDIVPH/R/KLP: MGR GAY ATH GTN CCN MRN YTR CCN             (SEQ ID NO:117)

for the two other sequences

3' primer for EYWIK/T: YKT DAT CCA RTA YTC                              (SEQ ID NO:118)

for Rhizomucor, Humicola and P.camenbertii

3' primer for PGVEYWIK/T: YKT DAT CCA RTA YTC NAC NCC NGG               (SEQ ID NO:119)

for Rhizopus

3' primer for AGEEYWIK/T: YKT DAT CCA RTA YTC YTC NCC NGC               (SEQ ID NO:120)

for Absidia

Set 7)
5' primer for EYWIK/T: GAR TAY TGG ATH AAR                              (SEQ ID NO:121)

or GAR TAY TGG ATH ACN                                                  (SEQ ID NO:122)

for Rhizomucor, Humicola and P.carnenbertii

5' primer for EYWIKSGT: GAR TAY TGG ATH AAR WSY GGN ACN                 (SEQ ID NO:123)

for Rhizopus

5' primer for EYWIKKDSS: GAR TAY TGG ATH AAR AAR GAY WSY WSY            (SEQ ID NO:124)

for Absidia

3' primer for DHLSY: RTA NGA/RCT YAR RTG RTC                            (SEQ ID NO:125)

for Absidia, Rhizopus and Rhizomucor sequences

3' primer for IPDIPDHLSY: RTA NGA/RCT YAR RTG RTC NGG DAT RTC NGG DAT   (SEQ ID NO:126)

for Humicola

3' primer for TDFEDHLSY: RTA NGA/RCT YAR RTG RTC YTC RAA RTC NGT        (SEQ ID NO:127)

for P. camenbertii
```

For the SOE-PCR the 5' primers from the first set of primers and the 3' primer for the last set of primers can be used. The SOE-PCR fragments can then be combined with a lipase 5' and 3' end, when the 5' and 3' ends have been generated by PCR.
The 5' end can be generated by PCR by using specific 5' primers (containing a sequence for the BamHI recognition site in the 5' end) for the 5' end of the genes of interest and using the complementary sequence from the 5' primer from the first set of primers as the 3' primer. The 3' end can be generated by PCR by using specific 3' primers (containing a sequence for the XbaI recognition site in the 5' end) for the 3' end of the genes of interest and the complementary sequence from the 3' primer from the last set of primers as the 5' primer.
A second SOE is then used to generate the complete sequence, by using the specific 5' and 3' primers from the genes of interest. The genes can then be cloned into the yeast vector pJSO26 as a BamHI-XbaI fragment (see WO 97/07205).

Example 3

The overall same method as described in example 2 can be used for amplification and recombination of PCR fragments of Pseudomonas lipases. The term "overall same method" denotes that it may be advantageous to use slightly different vectors as compared to example 2. Based on the sequence and primer information disclosed below it is a matter of routine for a person skilled in the art to modify the vectors etc. from example 2, in order to recombine below mentioned Pseudomonas lipases according to a shuffling method of the invention.

The *Pseudomonas lipases* mentioned below are aligned using the alignment program from Geneworks (using the following parameters:cost to open a gap=5, cost to lengthen a gap=25, Minimum Diagonal lLength=4, Maximum Diagonal Length=10, Consensus cutoff=50%).

*Pseudomonas lipases* (see FIG. 4):

*Pseudomonas aeruginosa* TE3285 (file ate3285d)

*Pseudomonas pseudoalcaligenes* M1 (Lipomax wt) (file pseudmid)

Pseudomonas sp. SD705 (mature)(file spsd7o5d)

*Pseudomonas wisconsinensis* (file wisconsd) Proteus vulgaris K80 (file provulgd) *Pseudomonas fragi* IFO 12049 (file fr12049d).

Suitable primers for shuffling of Pseudomonas lipases:

I=Inosin, Numbers refer to the numbers in the alignment(see FIG. 4), S means sense strand, the antisense oligonucleotide is of course also used:

```
109-131
S1: 5'-TA(C/T)CCNAT(C/T)(G/T)N(C/T)T(G/A)(G/A)(C/T)NCA(C/T)GG-3'        (SEQ ID NO:131)

250-269
S2: 5'-GA(G/A)(G/C)NNCGNGGNG(A/C)N(G/C)A(G/A)(T/C)T-3'                  (SEQ ID NO:132)

318-343
S3: 5'-GT(C/A)AA(C/T)(C/T)T(G/A)NTCGG(C/T)CA(C/T)AG(C/T)CANGG-3'        (SEQ ID NO:133)

607-628
S4: 5'-TNAA(C/T)(G/C/A)(G/C/A)(C/T/A)(A/C)(A/G)N(T/C)(A/T)(C/T)         (SEQ ID NO:134)
        CCN(C/T)(A/G)(T/GA)GG-3'

801-817
S5: 5'-AA(C/T)GA(C/T)GG(C/T)(C/A/T)TGGT(C/T/G)GG-3'                     (SEQ ID NO:135)

871-890
S6: 5'-CA(C/T)(C/G)T(C/G)GA(C/T)(G/A)(A/C/T)(G/C)(G/A)T(G/C/A)AACCA-3'  (SEQ ID NO:136)
```

---

What is claimed is:

1. A method for shuffling heterologous sequences, comprising the steps of:
   (a) identifying at least one conserved region between the heterologous sequences to be shuffled;
   (b) generating primers directed to the conserved region(s) identified in step (a); and
   (c) generating DNA fragments with the use of the primers generated in step (b) and the heterologous sequences of step (a) as templates, wherein shuffled sequences are generated.

2. The method of claim 1, further comprising the steps of:
   (d) expressing proteins encoded by the shuffled sequences generated in step (c); and
   (e) screening or selecting the expressed proteins for a protein having a desired activity.

3. The method of claim 1, wherein the primers of step (b) are directed to a DNA sequence having a homologous overlap of at least 10 bp within the conserved region.

4. The method of claim 1, wherein the primers of step (b) are directed to a DNA sequence having a homologous overlap of at least 15 bp within the conserved region.

5. The method of claim 1, wherein the primers of step (b) are directed to a DNA sequence having a homologous overlap of at least 20 bp within the conserved region.

6. The method of claim 1, wherein the heterologous sequences encode an enzyme.

7. The method of claim 6, wherein the enzyme is one of a protease, cellulase, phytase, oxidase, cutinase, or a lipase.

8. The method of claim 7, wherein the protease is a serine protease.

9. The method of claim 8, wherein the serine protease is a subtilase.

10. A method for shuffling more than one heterologous sequences, comprising the steps of:
    (a) identifying at least one conserved region between the heterologous sequences to be shuffled, wherein a conserved region of one heterologous sequence has at least 80% identity to the conserved region of another heterologous sequence;
    (b) generating primers directed to the conserved region(s) identified in step (a);
    (c) generating DNA fragments with the use of the primers generated in step (b); and
    (d) shuffling the DNA fragments generated in step (c).

11. The method of claim 10, further comprising the steps of:
    (e) expressing proteins encoded by the shuffled sequences generated in step (c); and
    (f) screening or selecting the expressed proteins for a protein having a desired activity.

12. The method of claim 10, wherein a conserved region of one heterologous sequence has at least 90% identity to the conserved region of another heterologous sequence.

13. The method of claim 10, wherein a conserved region of one heterologous sequence has at least 95% identity to the conserved region of another heterologous sequence.

14. A method for shuffling more than one heterologous sequences, comprising the steps of:
    (a) identifying at least one conserved region between the heterologous sequences to be shuffled, wherein a conserved region of one heterologous sequence has at least 80% identity to the conserved region of another heterologous sequence;
    (b) generating primers directed to the conserved region(s) identified in step (a), wherein the primers are directed to a DNA sequence having a homologous overlap of at least 10 bp within the conserved region;
    (c) generating DNA fragments with the use of the primers generated in step (b); and
    (d) shuffling the DNA fragments generated in step (c).

15. A method for shuffling heterologous DNA sequences of interest having at least one conserved region, the method comprising the steps of:
    (a) identifying at least one conserved region in at least two heterologous DNA sequences;
    (b) constructing at least a first and a second set of PCR primers, wherein each set comprises a sense and an anti-sense primer, and defines a DNA sequence having a homologous overlap of at least 10 bp within the conserved region of the heterologous DNA sequence of step (a),
    wherein the first set of PCR primers comprises primer A and A', primer A is directed to a sequence region 5' of the conserved region and primer A' is directed to one of (i) a sequence 3' of the conserved region, or (ii) a sequence partially within the conserved region, and
    wherein the second set of PCR primers comprises primer B and B', primer B is directed to one of (i) a sequence 3' of the conserved region, or (ii) a sequence partially within the conserved region, and primer B' is directed to a sequence 3' of the conserved region;
    (c) amplifying at least one of the heterologous DNA sequences of step (a) with the first and second primer sets of step (b); and
    (d) generating shuffled DNA fragments of the amplified DNA sequences of step (c).

16. The method of claim 15, further comprising the steps of:
    (e) expressing proteins encoded by the shuffled sequences generated in step (d); and
    (f) screening or selecting the expressed proteins for a protein having a desired activity.

17. The method of claim 15, wherein the heterologous sequences encode an enzyme.

18. The method of claim 17, wherein the enzyme is a protease or a lipase.

19. The method of claim 18, wherein the protease is a serine protease.

20. The method of claim 19, wherein the serine protease is a subtilase.

21. The method of claim 1, wherein the conserved region(s) are flanking sequences.

22. The method of claim 1, wherein the heterologous sequences to be shuffled comprise a partial sequence of at least 40 basepairs in length not having more than 90% sequence identity.

23. The method of claim 22, wherein the heterologous sequences to be shuffled comprise a partial sequence of at least 40 basepairs in length not having more than 95% sequence identity.

24. The method of claim 1, wherein the heterologous sequences to be shuffled are obtained from different species.

* * * * *

SEQUENCE LISTING (1) GENERAL INFORMATION:

(iii) NUMBER OF SEQUENCES: 136

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:1:

GAGGAGGGAA ACCGAATGAG GAAAAAGAGT TTTTGG      36

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (xi) SEQUENCE DESCRIPTION: SEQ ID NO:2:

CGCGGTCGGG TACCGTTTGC GCCAAGGCAT G      31

(2) INFORMATION FOR SEQ ID NO:3:

(i) SEQUENCE CHARACTERISTICS:
      (A) LENGTH: 36 base pairs

```
        (B) TYPE: nucleic acid
        (C) STRANDEDNESS: single
        (D) TOPOLOGY: linear (xi) SEQUENCE DESCRIPTION: SEQ ID NO:3:

GAGGAGGGAA ACCGAATGAG AGGCAAAAAA GTATGG                                 36

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:4:

CGCGGTCGGG TACCGACTGC GCGTACGCAT G                                      31

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:5:

GAGGAGGGAA ACCGAATGAG ACAAAGTCTA AAAGTTATG                               39

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:6:

CGCGGTCGGG TACCGTTTGA CTGATGGTTA CTTC                                    34

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

GAGGAGGGAA ACCGAATGAA GAAACCGTTG GGG                                     33

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:8:

CGCGGTCGGG TACCGATTGC GCCATTGTCG TTAC                                    34

(2) INFORMATION FOR SEQ ID NO:9:

(i) SEQUENCE CHARACTERISTICS:
        (A) LENGTH: 36 base pairs
        (B) TYPE: nucleic acid
```

```
        (C) STRANDEDNESS: single
        (D) TOPOLOGY: linear (xi) SEQUENCE DESCRIPTION: SEQ ID NO:9:

GAGGAGGGAA ACCGAATGAA GTTCAAAAAA ATAGCC                                    36

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:10:

CGCGGTCGGG TACCGCAGAA TAGTAAGGGT CATTC                                     35

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:11:

CGACGGCCAG CATTGG                                                          16

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

CATTCGGTTT CCCTCCTC                                                        18

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

CTTTGATACG TTTAAACTAC C                                                    21

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:14:

CGCGGTCGGG TACCG                                                           15

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
```

(D) TOPOLOGY: linear (xi) SEQUENCE DESCRIPTION: SEQ ID NO:15:

CCGGCGCAGG CGGTACCTRS GGATWCCRTM AAGC                              34

(2) INFORMATION FOR SEQ ID NO:16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:16:

CCGGCGCAGG CGGTACCTRS GGATWCAWWC ATWATAC                           37

(2) INFORMATION FOR SEQ ID NO:17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:17:

GTTCCGCACR TGGTCC                                                  16

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:18:

GGACCAYGTG CGGAAC                                                  16

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:19:

GCCCACTSAK CCGYTAC                                                 17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:20:

GCCCACTSAK CCTYGGC                                                 17

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:21:

GCCCATSRAK CCKRCWAT                                                     18

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:22:

GTARCGGMTS AGTGGGC                                                      17

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:23:

GCCRAGGMTS AGTGGGC                                                      17

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:24:

TWGCYCAAGG WWTSATGKR                                                    19

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

TWGCTCAAGG HHTHSARTGG                                                   20

(2) INFORMATION FOR SEQ ID NO:26:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:26:

GCGCACACAS ACCC                                                         14

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

GCYSCWAYWA MAGWAYAYCA                                                    20

(2) INFORMATION FOR SEQ ID NO:28:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:28:

GGGTSTGTGT GCGC                                                          14

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:29:

TGRTRTWCTM KTWRTWGSRG C                                                  21

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:30:

GBCCACRYTG ARAAWGAG                                                      18

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:31:

GBCCRTACTG GARAARCTG                                                     19

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:32:

GKCCATACKK AGARAARYTT G                                                  21

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:33:

GKRCCATACK KAGARAAGYT TG                                          22

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:34:

CTCWTTYTCA RYGTGGVC                                               18

(2) INFORMATION FOR SEQ ID NO:35:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:35:

CAGYTTYTCC AGTAYGGVC                                              19

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:36:

CAAGYTTCTC TMMGTATGGS MC                                          22

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:37:

CAAGTTTCTC TCAGTATGGG AC                                          22

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:38:

GGGWGCCATG AYGTCC                                                 16

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:39:

```
GGAGTAGCCA TGAGTWCC                                                   18

(2) INFORMATION FOR SEQ ID NO:40:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (xi) SEQUENCE DESCRIPTION: SEQ ID NO:40:

GGACRTCATG GCWCCC                                                     16

(2) INFORMATION FOR SEQ ID NO:41:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (xi) SEQUENCE DESCRIPTION: SEQ ID NO:41:

GGWACTCATG GCAWCCC                                                    17

(2) INFORMATION FOR SEQ ID NO:42:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (xi) SEQUENCE DESCRIPTION: SEQ ID NO:42:

CGGCCCCGAC GCGTTTACYG RYGCSYYTSR C                                    31

(2) INFORMATION FOR SEQ ID NO:43:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:43:

CGGCCCCGAC GCGTTTATCK TRYGCYTYWG                                      30

(2) INFORMATION FOR SEQ ID NO:44:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (xi) SEQUENCE DESCRIPTION: SEQ ID NO:44:

CGGCCCCGAC GCGTTTATCK TRCGCGCTYT GMRTT                                35

(2) INFORMATION FOR SEQ ID NO:45:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (xi) SEQUENCE DESCRIPTION: SEQ ID NO:45:

CGGCCCCGAC GCGTTTATCT TACGGCAGCC TCAGC                                35
```

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:46:

CCGGCGCAGG CGGTACC                                                  17

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:47:

CGGCCCCGAC GCGTTTA                                                  17

(2) INFORMATION FOR SEQ ID NO:48:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:48:

GGCGCAGGCG GTAC                                                     14

(2) INFORMATION FOR SEQ ID NO:49:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:49:

GCCCCGACGC GTTTA                                                    15

(2) INFORMATION FOR SEQ ID NO:50:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:50:

CGCAGGCGGT AC                                                       12

(2) INFORMATION FOR SEQ ID NO:51:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:51:

CCCGACGCGT T                                                        11

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:52:

TAYTGYMGRA CNGTNATHCC NGG                                                        23

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:53:

TAYTGYMGRA GYGTNGTNCC NGG                                                        23

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:54:

TAYTGYMGRT CNGTNGTNCC NGG                                                        23

(2) INFORMATION FOR SEQ ID NO:55:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:55:

NSWNCCYCKR AANAC                                                                        15

(2) INFORMATION FOR SEQ ID NO:56:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:56:

GTNTTYMGRG GNWSN                                                                        15

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:57:

RAANCCYTTR TGNACYTT                                                              18

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:58:

RAANCCNGCR TGNACYTT                                             18

(2) INFORMATION FOR SEQ ID NO:59:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:59:

AARGTNCAYA ARGGNTTY                                             18

(2) INFORMATION FOR SEQ ID NO:60:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:60:

AARGTNCAYG CNGGNTTY                                             18

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:61:

CCNCCYARNG ARTGNCCNGT NAC                                       23

(2) INFORMATION FOR SEQ ID NO:62:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:62:

CCNCCYARRC TRTGNCCNGT NAC                                       23

(2) INFORMATION FOR SEQ ID NO:63:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:63:

GTNACNGGNC AYTCNYTRGG NGG                                       23

(2) INFORMATION FOR SEQ ID NO:64:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (xi) SEQUENCE DESCRIPTION: SEQ ID NO:64:

GTNACNGGNC AYAGYYTRGG NGG                                              23

(2) INFORMATION FOR SEQ ID NO:65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:65:

RTGYARRAAN CCRAA                                                       15

(2) INFORMATION FOR SEQ ID NO:66:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:66:

TTYGGNTTYY TRCAY                                                       15

(2) INFORMATION FOR SEQ ID NO:67:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:67:

NGTRAANGGN ACDAT                                                       15

(2) INFORMATION FOR SEQ ID NO:68:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:68:

TGYCCNGARG TNGAR                                                       15

(2) INFORMATION FOR SEQ ID NO:69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:69:

NCCYCKRAAN GMYARNAC                                                    18

(2) INFORMATION FOR SEQ ID NO:70:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:70:

GTNYTRKCNT TYMGRGGN                                                 18

(2) INFORMATION FOR SEQ ID NO:71:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:71:

CCANGANGAN GTRAANCC                                                 18

(2) INFORMATION FOR SEQ ID NO:72:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:72:

CCARSWRSWC CARAANCC                                                 18

(2) INFORMATION FOR SEQ ID NO:73:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:73:

GGNTTYACNT CNTCNTGG                                                 18

(2) INFORMATION FOR SEQ ID NO:74:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:74:

GGNTTYTGGW SYWSYTGG                                                 18

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:75:

NGCNSCNCCY ARNGARTGNC C                                             21

(2) INFORMATION FOR SEQ ID NO:76:

(i) SEQUENCE CHARACTERISTICS:

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:76:

NGCNSCNCCY ARRCTRTGNC C                                              21

(2) INFORMATION FOR SEQ ID NO:77:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:77:

GGNCAYTCNY TRGGNGSNGC N                                              21

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:78:

GGNCAYAGYY TRGGNGSNGC N                                              21

(2) INFORMATION FOR SEQ ID NO:79:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:79:

RTTNCCNACY CKNGG                                                     15

(2) INFORMATION FOR SEQ ID NO:80:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:80:

CCNMGRGTNG GNAAY                                                     15

(2) INFORMATION FOR SEQ ID NO:81:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:81:

RTCRTTNGTR TGNGT                                                     15

(2) INFORMATION FOR SEQ ID NO:82:

(i) SEQUENCE CHARACTERISTICS:
        (A) LENGTH: 15 base pairs (B) TYPE: nucleic acid
        (C) STRANDEDNESS: single
        (D) TOPOLOGY: linear (xi) SEQUENCE DESCRIPTION: SEQ ID NO:82:

ACNCAYACNA AYGAY                                                    15

(2) INFORMATION FOR SEQ ID NO:83:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:83:

DATCCARTAY TCNGG                                                    15

(2) INFORMATION FOR SEQ ID NO:84:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:84:

CCNGARTAYT GGATH                                                    15

(2) INFORMATION FOR SEQ ID NO:85:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:85:

RAARTACCAD AKRTGNGC                                                 18

(2) INFORMATION FOR SEQ ID NO:86:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:86:

GCNAMYKCNT AYTGYMG                                                  17

(2) INFORMATION FOR SEQ ID NO:87:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:87:

GCNAMYKCNT AYTGYGGNAA RAAYAAYGAY GC                                 32

(2) INFORMATION FOR SEQ ID NO:88:

(i) SEQUENCE CHARACTERISTICS:
        (A) LENGTH: 32 base pairs
        (B) TYPE: nucleic acid (C) STRANDEDNESS: single
                (D) TOPOLOGY: linear (xi) SEQUENCE DESCRIPTION: SEQ ID NO:88:

GCNAMYKCNT AYTGYGARGC NGAYTAYACN GC                                    32

(2) INFORMATION FOR SEQ ID NO:89:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:89:

RTADATNGTY TTYTS                                                       15

(2) INFORMATION FOR SEQ ID NO:90:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:90:

RTADATNGTY TTYTSNGTRT TRTCYARNGC                                       30

(2) INFORMATION FOR SEQ ID NO:91:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:91:

RTADATNGTY TTYTSNGTRT GRTCNACNGC                                       30

(2) INFORMATION FOR SEQ ID NO:92:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:92:

SARAARACNA THTAY                                                       15

(2) INFORMATION FOR SEQ ID NO:93:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:93:

SARAARACNA THTAYYTRKC NTTYMGRGGN                                       30

(2) INFORMATION FOR SEQ ID NO:94:

(i) SEQUENCE CHARACTERISTICS:
                (A) LENGTH: 18 base pairs
                (B) TYPE: nucleic acid
                (C) STRANDEDNESS: single (D) TOPOLOGY: linear (xi) SEQUENCE DESCRIPTION: SEQ ID NO:94:

RAANCCYTTR TGNACYTT                                                    18

(2) INFORMATION FOR SEQ ID NO:95:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:95:

RAANCCNGCR TGNACYTT                                                    18

(2) INFORMATION FOR SEQ ID NO:96:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:96:

RAANCCYTTR TGNACYTTRC ANCCNGARCA DAT                                   33

(2) INFORMATION FOR SEQ ID NO:97:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:97:

RAANCCNGCR TGNACYTTRC ANCCNGARCA DAT                                   33

(2) INFORMATION FOR SEQ ID NO:98:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:98:

RAANCCYTTR TGNACYTTRC ANCCRTCRCA YAR                                   33

(2) INFORMATION FOR SEQ ID NO:99:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:99:

RAANCCNGCR TGNACYTTRC ANCCRTCRCA YAR                                   33

(2) INFORMATION FOR SEQ ID NO:100:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:100:

AARGTNCAYA ARGGNTTY                                                           18

(2) INFORMATION FOR SEQ ID NO:101:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:101:

AARGTNCAYG CNGGNTTY                                                           18

(2) INFORMATION FOR SEQ ID NO:102:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:102:

AARGTNCAYA ARGGNTTYAC NTCNTCNTGG                                               30

(2) INFORMATION FOR SEQ ID NO:103:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:103:

AARGTNCAYG CNGGNTTYAC NTCNTCNTGG                                               30

(2) INFORMATION FOR SEQ ID NO:104:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:104:

AARGTNCAYA ARGGNTTYTG GWSYWSYTGG                                               30

(2) INFORMATION FOR SEQ ID NO:105:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:105:

AARGTNCAYG CNGGNTTYTG GWSYWSYTGG                                               30

(2) INFORMATION FOR SEQ ID NO:106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:106:

NGCNSCNCCY ARNGARTGNC C                                              21

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:107:

NGCNSCNCCY ARRCTRTGNC C                                              21

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:108:

GGNCAYTCNY TNGGNGSNGC N                                              21

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:109:

GGNCAYAGYY TNGGNGSNGC N                                              21

(2) INFORMATION FOR SEQ ID NO:110:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:110:

RTYNCCNACY CKNGG                                                     15

(2) INFORMATION FOR SEQ ID NO:111:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:111:

RTYNCCNACY CKNGGYTGNC CYTGNGT                                        27

(2) INFORMATION FOR SEQ ID NO:112:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:112:

```
CCNMGRGTNG GNRAY                                                              15

(2) INFORMATION FOR SEQ ID NO:113:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:113:

CCNMGRGTNG GNRAYCCNGC NTTYGCN                                                 27

(2) INFORMATION FOR SEQ ID NO:114:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:114:

YKNGGNACDA TRTCYCK                                                            17

(2) INFORMATION FOR SEQ ID NO:115:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:115:

YKNGGNACDA TRTCYCKNGT RTGNGTRAW                                               29

(2) INFORMATION FOR SEQ ID NO:116:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:116:

MGRGAYATHG TNCCNMR                                                            17

(2) INFORMATION FOR SEQ ID NO:117:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:117:

MGRGAYATHG TNCCNMRNYT RCCN                                                    24

(2) INFORMATION FOR SEQ ID NO:118:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:118:
```

```
YKTDATCCAR TAYTC                                                         15

(2) INFORMATION FOR SEQ ID NO:119:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:119:

YKTDATCCAR TAYTCNACNC CNGG                                               24

(2) INFORMATION FOR SEQ ID NO:120:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:120:

YKTDATCCAR TAYTCYTCNC CNGC                                               24

(2) INFORMATION FOR SEQ ID NO:121:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:121:

GARTAYTGGA THAAR                                                         15

(2) INFORMATION FOR SEQ ID NO:122:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:122:

GARTAYTGGA THACN                                                         15

(2) INFORMATION FOR SEQ ID NO:123:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:123:

GARTAYTGGA THAARWSYGG NACN                                               24

(2) INFORMATION FOR SEQ ID NO:124:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (xi) SEQUENCE DESCRIPTION: SEQ ID NO:124:

GARTAYTGGA THAARAARGA YWSYWSY                                            27
```

(2) INFORMATION FOR SEQ ID NO:125:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:125:

RTANGAYARR TGRTC                                            15

(2) INFORMATION FOR SEQ ID NO:126:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:126:

RTARCTYARR TGRTC                                            15

(2) INFORMATION FOR SEQ ID NO:127:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:127:

RTANGAYARR TGRTCNGGDA TRTCNGGDAT                            30

(2) INFORMATION FOR SEQ ID NO:128:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:128:

RTARCTYARR TGRTCNGGDA TRTCNGGDAT                            30

(2) INFORMATION FOR SEQ ID NO:129:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:129:

RTANGAYARR TGRTCYTCRA ARTCNGT                              27

(2) INFORMATION FOR SEQ ID NO:130:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:130:

RTARCTYARR TGRTCYTCRA ARTCNGT                              27

(2) INFORMATION FOR SEQ ID NO:131:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:131:

TACTCCNATC TGTNCTTGAG ACTNCACTGG                                        30

(2) INFORMATION FOR SEQ ID NO:132:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:132:

GAGAGCNNCG NGGNGACNGC AGATCT                                              26

(2) INFORMATION FOR SEQ ID NO:133:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:133:

GTCAAACTCT TGANTCGGCT CACTAGCTCA NGG                                    33

(2) INFORMATION FOR SEQ ID NO:134:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:134:

TNAACTGCAG CACTAACAGN TCATCTCCNC TAGTGAGG                            38

(2) INFORMATION FOR SEQ ID NO:135:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:135:

AACTGACTGG CTCATTGGTC TGGG                                                  24

(2) INFORMATION FOR SEQ ID NO:136:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:136:

CACTCGTCGG ACTGAACTGC GATGCAAACC A                                    31